United States Patent
Bavali et al.

(10) Patent No.: US 11,499,919 B2
(45) Date of Patent: Nov. 15, 2022

(54) DETERMINING SUCROSE CONCENTRATION IN HONEY BASED ON FLUORESCENCE SPECTROSCOPY

(71) Applicants: Ali Bavali, Tehran (IR); Alireza Mashhadi, Tehran (IR); Amir Jafargholi, Tehran (IR); Mohsen Hashemi, Tehran (IR); Farzad Mokhtari, Tehran (IR)

(72) Inventors: Ali Bavali, Tehran (IR); Alireza Mashhadi, Tehran (IR); Amir Jafargholi, Tehran (IR); Mohsen Hashemi, Tehran (IR); Farzad Mokhtari, Tehran (IR)

(73) Assignee: AMIRKABIR UNIVERSITY OF TECHNOLOGY, Tehran (IR)

( * ) Notice: Subject to any disclaimer, the term of this patent is extended or adjusted under 35 U.S.C. 154(b) by 0 days.

(21) Appl. No.: 17/204,956

(22) Filed: Mar. 18, 2021

(65) Prior Publication Data
US 2021/0199589 A1  Jul. 1, 2021

(51) Int. Cl.
*G01N 21/64* (2006.01)
*G01J 3/44* (2006.01)
*G01N 33/02* (2006.01)
*G01N 23/20016* (2018.01)

(52) U.S. Cl.
CPC ........ *G01N 21/6486* (2013.01); *G01J 3/4406* (2013.01); *G01N 23/20016* (2013.01); *G01N 33/02* (2013.01)

(58) Field of Classification Search
CPC .. G01J 2003/4435; G01N 2021/16491; G01N 21/6486; G01N 23/20016
See application file for complete search history.

(56) References Cited

U.S. PATENT DOCUMENTS 10,900,892 B1 *  1/2021  Mackenzie  ............ G01N 21/31

OTHER PUBLICATIONS

Landulfo Silveira, "Determination of sucrose concentration in lemon-type soft drinks by dispersive Raman spectroscopy", 2009 (Year: 2009).*
Noriah Bidin, "Sugar Detection in Adulterated Honey via Fiber Optic Displacement Sensor for Food Industrial Applications", 2015 (Year: 2015).*
Emmanouil Orfanakis, "Optical spectroscopy methods combined with multivariate statistical analysis for the classification of Cretan thyme, multi-floral and honeydew honey" Mar. 2021 (Year: 2021).*

* cited by examiner

*Primary Examiner* — Maurice C Smith
(74) *Attorney, Agent, or Firm* — Bajwa IP Law Firm; Haris Zaheer Bajwa

(57) ABSTRACT

A method for determining sucrose concentration in honey. The method includes preparing a sample of honey, stimulating the sample by emitting a first laser beam on the sample in a first stimulation direction, detecting a fluorescence spectrum from a first fluorescence emission emitted from the sample in a first detection direction, detecting a first pair of fluorescence peaks and a second pair of peak wavelengths in the fluorescence spectrum, and determining a sucrose concentration based on one of the first pair and the second pair utilizing a database. The database includes a plurality of predetermined sucrose concentrations associated with the first pair or the second pair.

20 Claims, 11 Drawing Sheets

DETERMINING SUCROSE CONCENTRATION IN HONEY BASED ON FLUORESCENCE SPECTROSCOPY

CROSS-REFERENCE TO RELATED APPLICATION

This application claims the benefit of priority from U.S. Provisional Patent Application Ser. No. 62/991,079, filed on Mar. 18, 2020, and entitled "SYSTEM FOR DETERMINING THE SUCROSE CONCENTRATION IN HONEY BASED ON THE IMPACT OF SUCROSE MOLECULES ON SELF-ABSORPTION OF THE LASER INDUCED FLUORESCENCE BY FLAVONOIDS IN HONEY," which is incorporated herein by reference in its entirety.

TECHNICAL FIELD

The present disclosure generally relates to optical spectroscopy, and particularly, to fluorescence spectroscopy.

BACKGROUND

Honey is one of the oldest foods and natural remedies, and also one of the five important foods most widely exposed to fraud. This natural product contains carbohydrates, proteins, enzymes, vitamins, amino acids, dyes, water, and a variety of minerals. Low pH and existence of a variety of carbohydrates, flavonoids, hydrogen peroxide, phenolics, and terpenes in honey have made honey an effective anti-infectious and antibacterial substance.

Hydrocarbons make up about 90% of the weight of honey (excluding water). An important honey adulteration is adding excessive sucrose (more than 5 g in 100 g honey). Therefore, measurement of the sucrose concentration may be an important indicator of the purity of honey.

So far, various optical methods have been used to identify and quantify some honey components. For example, laser induced breakdown spectroscopy (LIBS) and fluorescence intensity measurements have been utilized to determine mineral elements and the botanical origin of honey, respectively. Furthermore, conventional fluorescence spectroscopy methods based on photoluminescence (PL) have been used to detect flavonoids and some botanical species. Although non-destructive, optical methods may be costly, and may be highly dependent on environmental conditions such as sample temperature. Moreover, these methods directly excite sucrose and therefore may not be used to quantify sucrose concentration in honey because other components of honey may also be simultaneously excited.

There is, therefore, a need for a non-destructive method that may accurately quantify sucrose concentration in honey. There is also a need for a low-cost system for determining sucrose concentration in honey with a robust performance in different environmental conditions.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for determining sucrose concentration in honey. An exemplary method may include preparing a sample of honey, stimulating the sample by emitting a first laser beam on the sample in a first stimulation direction, detecting a fluorescence spectrum from a first fluorescence emission emitted from the sample in a first detection direction, detecting a first pair of fluorescence peaks and a second pair of peak wavelengths in the first fluorescence spectrum, and determining a sucrose concentration based on one of the first pair and the second pair utilizing a database. An exemplary sample may be associated with a floral source. An exemplary first laser beam may include a laser wavelength. An exemplary laser wavelength may be set in a range of 390 nm and 410 nm. An exemplary spectrometer may be utilized for detecting the fluorescence spectrum.

In an exemplary embodiment, detecting the first pair of fluorescence peaks may include detecting a first fluorescence peak of the first pair and a second fluorescence peak of the first pair in the fluorescence spectrum. Each of an exemplary first fluorescence peak and an exemplary second fluorescence peak may include a respective local maximum fluorescence intensity in the fluorescence spectrum. In an exemplary embodiment, detecting the second pair of peak wavelengths may include detecting a first peak wavelength of the second pair and a second peak wavelength of the second pair in the fluorescence spectrum. An exemplary first peak wavelength may be associated with the first fluorescence peak and an exemplary second peak wavelength may be associated with the second fluorescence peak. In an exemplary embodiment, the first peak wavelength may be smaller than the second peak wavelength.

In an exemplary embodiment, the first detection direction may make a detection angle with the stimulation direction. In an exemplary embodiment, the database may include a plurality of predetermined sucrose concentrations associated with the one of the first pair and the second pair. In an exemplary embodiment, preparing the sample may include depositing the sample in a cylindrical container. A diameter of a cross-section of an exemplary cylindrical container may be equal to or larger than a width of the first laser beam.

In an exemplary embodiment, detecting the fluorescence spectrum may include setting the detection angle in a range of 20° and 90°, positioning a main axis of a tip of an optical fiber in the first detection direction, capturing the first fluorescence emission by the optical fiber, and sending the first fluorescence emission to the spectrometer via the optical fiber. An exemplary goniometer may be utilized for setting the detection angle and an exemplary moving table may be utilized for positioning the main axis.

In an exemplary embodiment, determining the sucrose concentration may include calculating a ratio of the first fluorescence peak to the second fluorescence peak and extracting the sucrose concentration from the database by finding a first predetermined sucrose concentration of the plurality of predetermined sucrose concentrations in the database. An exemplary first predetermined sucrose concentration may be associated with the ratio. In an exemplary embodiment, determining the sucrose concentration may further include extracting the sucrose concentration from the database by finding a second predetermined sucrose concentration of the plurality of predetermined sucrose concentrations in the database. In an exemplary embodiment, the second predetermined sucrose concentration may be associated with the first peak wavelength. In an exemplary embodiment, determining the sucrose concentration may further include estimating the sucrose concentration by averaging first predetermined sucrose concentration and the second predetermined sucrose concentration.

In an exemplary embodiment, determining the sucrose concentration utilizing the database may include generating the database utilizing a standard sample of honey. An exemplary standard sample may be made from the floral source. In an exemplary embodiment, generating the database may include producing a sucrose-added sample of honey by adding a predetermined sucrose concentration of the plurality of predetermined sucrose concentrations to the standard sample, stimulating the sucrose-added sample by emitting a second laser beam on the sucrose-added sample in a second stimulation direction, detecting a standard fluorescence spectrum of a plurality of standard fluorescence spectra from a second fluorescence emission, and extracting the database from the plurality of standard fluorescence spectra. An exemplary laser beam may include the laser wavelength. An exemplary second fluorescence emission may be emitted from the sucrose-added sample in a second detection direction. An exemplary second detection direction may make the detection angle with the second stimulation direction. In an exemplary embodiment, each of the plurality of standard fluorescence spectra may be associated with a respective predetermined sucrose concentration of the plurality of predetermined sucrose concentrations. An exemplary spectrometer may be utilized for detecting the standard fluorescence spectrum.

In an exemplary embodiment, extracting the database may include detecting a standard peak pair of a plurality of standard peak pairs in the standard fluorescence spectrum and calculating a ratio of the first standard peak to the second standard peak. An exemplary standard peak pair may include a first standard peak and a second standard peak. Each of an exemplary first standard peak and an exemplary second standard peak may include a respective local maximum fluorescence intensity in the standard fluorescence spectrum. In an exemplary embodiment, the ratio of the first standard peak to the second standard peak may be associated with the predetermined sucrose concentration.

In an exemplary embodiment, extracting the database may further include extracting a first standard wavelength and a second standard wavelength from the standard fluorescence spectrum. An exemplary first standard wavelength may be associated with the first standard peak and an exemplary second standard wavelength may be associated with the second standard peak. In an exemplary embodiment, the first standard wavelength may be smaller than the second standard wavelength.

Other exemplary systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the claims herein.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Herein is disclosed an exemplary method and system for quantifying sucrose concentration in a sample of honey. To this end, the sample may be stimulated by an exemplary laser beam. Upon stimulation, certain components in honey (i.e., flavonoids) may be excited and may produce fluorescence emission. An exemplary emitted fluorescence from the sample may be detected by a spectrometer. An exemplary spectrometer may be positioned at a predetermined detection angle to detect a pair of peaks in a detected fluorescence spectrum. Exemplary pair of peaks may be detected of an exemplary fluorescence spectrum of the detected emission at two different wavelengths. An exemplary ratio of the peaks may vary according to a level of sucrose concentration. Therefore, a level of sucrose concentration may be obtained based on an exemplary ratio of the peaks. Hence, the ratio of the peaks may be calculated and compared with a set of predetermined values in a given exemplary database to find a sucrose concentration level that may correspond to the calculated ratio. An exemplary database may be provided prior to stimulating the sample from different honey samples with different levels of sucrose concentration. Consequently, the sucrose concentration in the sample of honey may be determined by comparing data that is extracted from the sample with a respective data of the database.

Figure 1A:
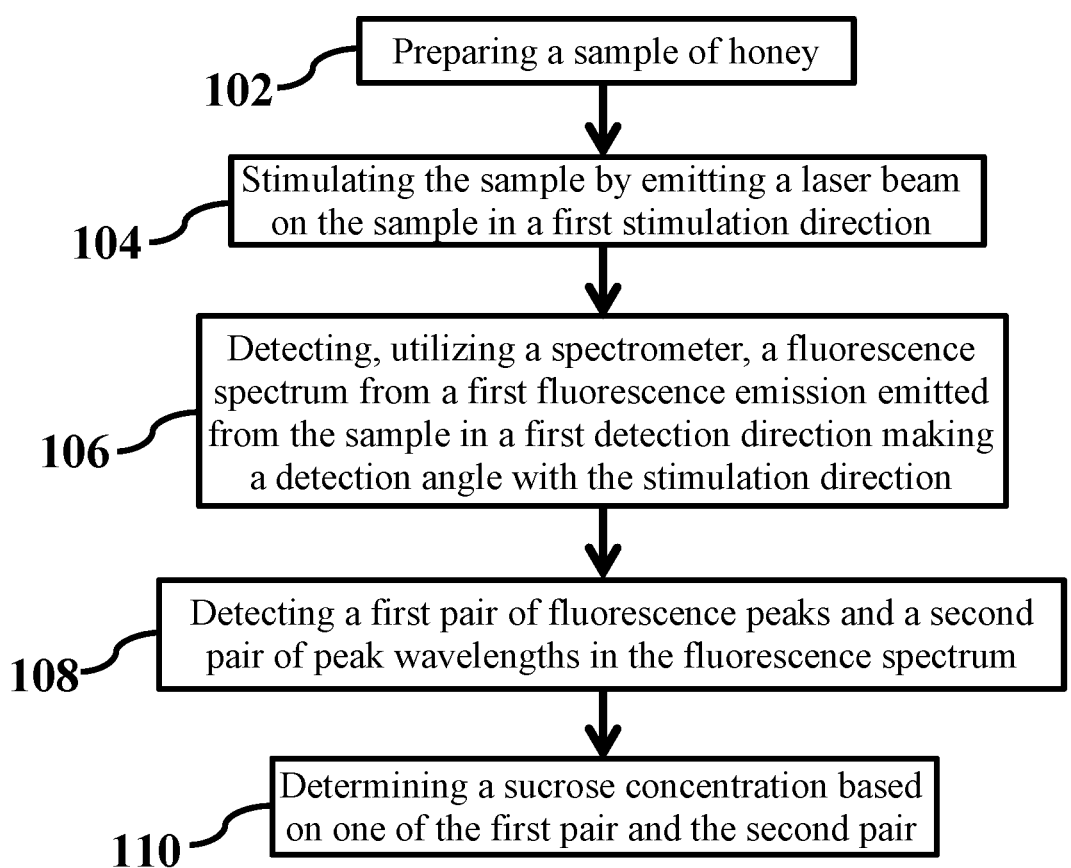
FIG. 1A shows a flowchart of a method for determining sucrose concentration in honey, consistent with one or more exemplary embodiments of the present disclosure.

FIG. 1A shows a flowchart of a method for determining sucrose concentration in honey, consistent with one or more exemplary embodiments of the present disclosure. An exemplary method 100 may include preparing a sample of honey (step 102), stimulating the sample by emitting a first laser beam on the sample in a first stimulation direction (step 104), detecting a fluorescence spectrum from a first fluorescence emission emitted from the sample in a first detection direction (step 106), detecting a first pair of fluorescence peaks and a second pair of peak wavelengths in the fluorescence spectrum (step 108), and determining a sucrose concentration based on one of the first pair and the second pair utilizing a database (step 110). An exemplary database may include a plurality of predetermined sucrose concentrations that may be associated with the first pair or the second pair.

Figure 2:
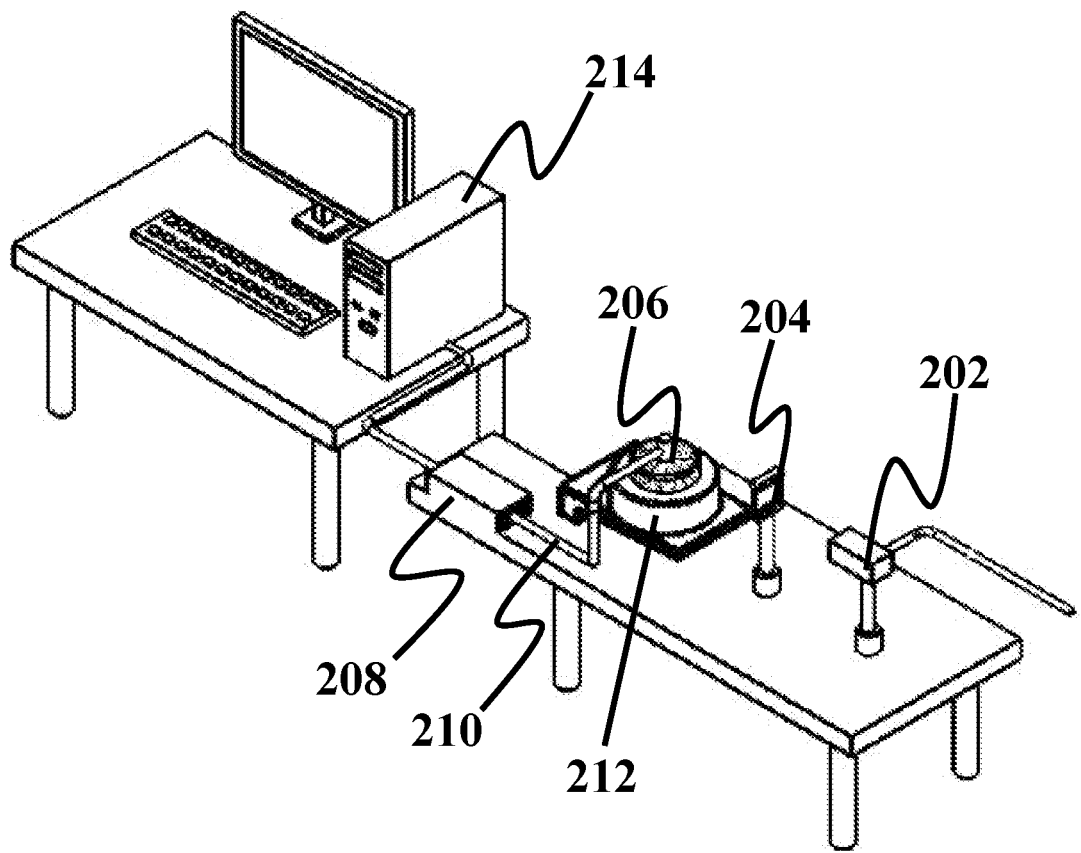
FIG. 2 shows a schematic of a system for determining sucrose concentration in honey, consistent with one or more exemplary embodiments of the present disclosure.

FIG. 2 shows a schematic of a system for determining sucrose concentration in honey, consistent with one or more exemplary embodiments of the present disclosure. In an exemplary embodiment, different steps of method 100 may be implemented utilizing an exemplary system 200. In an exemplary embodiment, system 200 may include a laser 202, an optical filter 204, a cylindrical container 206, a spectrometer 208, an optical fiber 210, a moving table 212, and a computer system 214. Further detail with respect to each of the above mentioned elements is provided below.

For further detail with respect to step 102, in an exemplary embodiment, preparing the sample may include depositing the sample in cylindrical container 206. An exemplary sample may be associated with a floral source. In an exemplary embodiment, the sample may be labeled with a given floral source that may specify the origin of the sample of honey. Different specifications of honey (such as sucrose concentration) may be identified based on the floral source of honey. Therefore, in an exemplary, method 100 may be utilized to determine whether an additional amount of sucrose may have been added to the sample and/or how much extra sucrose the sample may include. In other words, the purity of sample may be evaluated utilizing method 100.

Figure 3:
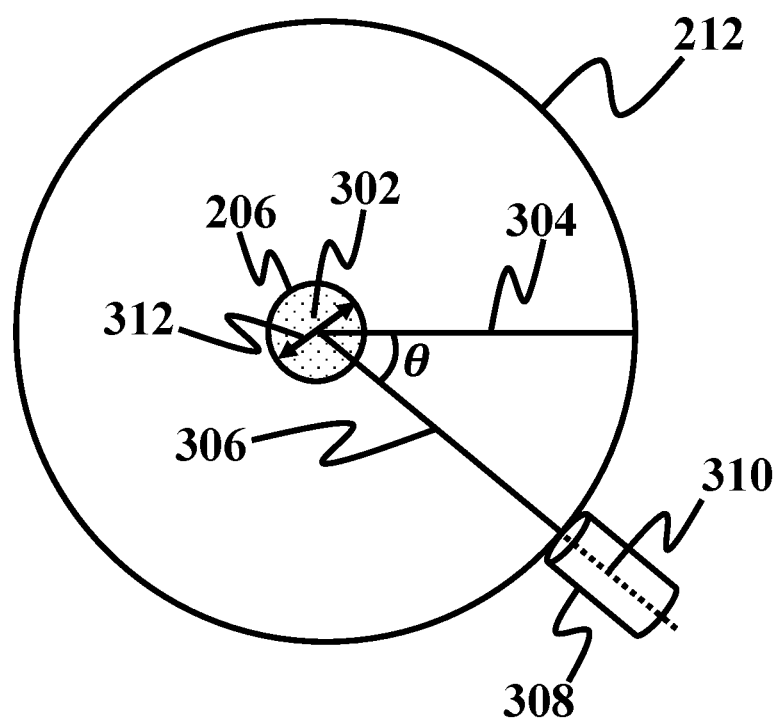
FIG. 3 shows a schematic of a sample of honey stimulated by a laser beam, consistent with one or more exemplary embodiments of the present disclosure.

For further detail with respect to step 104, FIG. 3 shows a schematic of a sample of honey stimulated by a laser beam, consistent with one or more exemplary embodiments of the present disclosure. In an exemplary embodiment, step 104 may include stimulating a sample 302 of honey by emitting a first laser beam on sample 302 in a first stimulation direction 304. In an exemplary embodiment, laser 202 may be utilized to emit the first laser beam. In an exemplary embodiment, laser 202 may include laser diode that may be configured to emit a violet laser beam (i.e., a laser beam with a wavelength between 360 and 480 nanometers). In an exemplary embodiment, the power of laser 202 may be set to about 20-60 mW so that the first laser beam intensity may be high enough to stimulate sample 302. In an exemplary embodiment, sample 302 may include flavonoids, which are a class of organic compounds found in plants, and hence may be an essential component of the floral source of honey. Upon stimulation of sample 302, the flavonoids in sample 302 may produce fluorescence emission. An exemplary fluorescence emission from sample 302 may pass through different materials in honey, including sucrose, which may affect a pattern of fluorescence emission by reabsorbing (i.e., self-absorption) laser-induced fluorescence emission of flavonoids in honey. Different sucrose concentrations may have different self-absorption rates and thus different impacts on the pattern of fluorescence emission. Therefore, an exemplary fluorescence emission from flavonoids in sample 302 may be utilized to identify the level of sucrose concentration in sample 302.

An exemplary first laser beam may include a laser wavelength. In order for flavonoids to produce fluorescence emission, an exemplary laser wavelength may have to be set in a specific range so that the first laser beam may be absorbed by the flavonoids in sample 302. However, in an exemplary embodiment, emissions from other materials in honey may have to be avoided since they may interfere with flavonoid emissions. In an exemplary embodiment, the laser wavelength may be set in a range of 390 nm and 410 nm.

In an exemplary embodiment, step 106 may include detecting a fluorescence spectrum from a first fluorescence emission emitted from sample 302 in a first detection direction 306. In an exemplary embodiment, first detection direction 306 may make a detection angle θ with stimulation direction 304. In an exemplary embodiment, spectrometer 208 may be utilized for detecting the first fluorescence emission.

Referring to FIGS. 2 and 3, in an exemplary embodiment, optical filter 204 may be utilized for setting a width (i.e., spot size) of the first laser beam equal to or smaller than a diameter 312 of a cross-section of cylindrical container 206 (for example, about 1 cm). In other words, in an exemplary embodiment, diameter 312 may be equal to or larger than the width of the first laser beam. In an exemplary embodiment, decreasing the spot size may cause the first laser beam to focus on a small portion of sample 302, resulting in an excitation of a small number of molecules of honey. As a result, in an exemplary embodiment, a sufficient number of unexcited molecules may remain in first detection direction 306 to reabsorb the first fluorescence emission, so that the impact of sucrose concentration on the fluorescence spectrum may be significant enough for determining the sucrose concentration in sample 302.

Figure 1B:
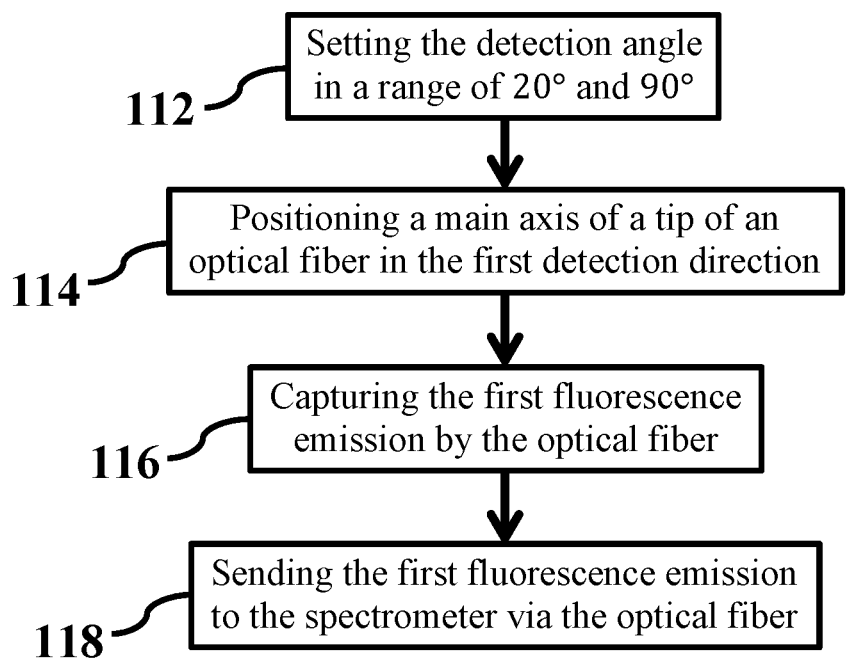
FIG. 1B shows a flowchart for detecting a fluorescence spectrum from a first fluorescence emission emitted from a sample, consistent with one or more exemplary embodiments of the present disclosure.

In further detail with regards to step 106, FIG. 1B shows a flowchart for detecting a fluorescence spectrum from a first fluorescence emission emitted from a sample, consistent with one or more exemplary embodiments of the present disclosure. Referring to FIGS. 1B, 2, and 3, in an exemplary embodiment, detecting the fluorescence spectrum may include setting detection angle θ in a range of 20° and 90° (step 112), positioning a main axis of a tip of optical fiber 210 in first detection direction 306 (step 114), capturing the first fluorescence emission by optical fiber 210 (step 116), and sending the first fluorescence emission to spectrometer 208 via optical fiber 210 (step 118).

In further detail with regards to step 112, in an exemplary embodiment, moving table 212 may include a goniometer that may be utilized for setting detection angle $\theta$ in the range of 20° and 90°. In an exemplary embodiment, if detection angle $\theta$ is set too small (for example, smaller than 20°), the first fluorescence emission from sample 302 may not experience self-absorption because the fluorescence emission may pass through excited molecules in sample 302 that may be unable to reabsorb the fluorescence. On the other hand, in an exemplary embodiment, an excessive increase of detection angle $\theta$ (for example, more than 90°) may increase reabsorption of the first fluorescence emission so that an intensity of the fluorescence may become too low to be detected by spectrometer 208. In an exemplary embodiment, a detection angle of about 60° may result in an optimized fluorescence pattern for determining sucrose concentration in sample 302.

For further detail with respect to steps 114, 116, and 118, in an exemplary embodiment, optical fiber 210 may include a tip 308, as shown in FIG. 3. In an exemplary embodiment, tip 308 may have a main axis 310. In an exemplary embodiment, tip 308 may include an optical micro-component that may be carved on an end of optical fiber 210 to reconfigure fluorescence emission that may enter optical fiber 210. In an exemplary embodiment, step 114 may include positioning main axis 310 in first detection direction 306. In an exemplary embodiment, moving table 212 may be utilized for positioning main axis 310 in first detection direction 306. As a result, in an exemplary embodiment, the first fluorescence emission may be captured by optical fiber 210 at detection angle $\theta$ in step 116. In an exemplary embodiment, optical fiber 210 may be connected to spectrometer 208 to send the captured fluorescence to spectrometer 208 in step 118.

Figure 4:
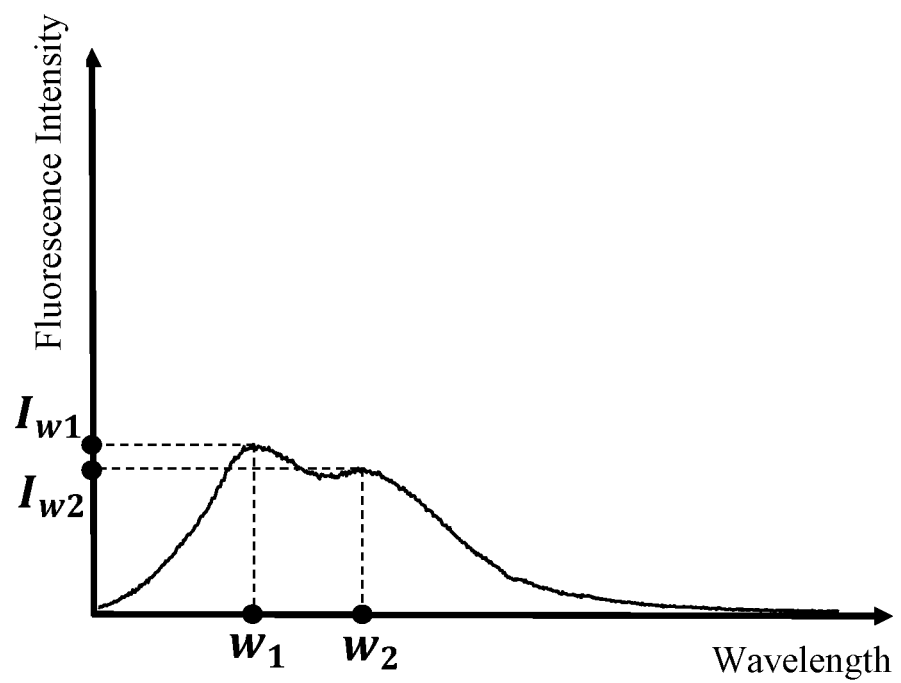
FIG. 4 shows a fluorescence spectrum, consistent with one or more exemplary embodiments of the present disclosure.

In further detail regarding step 108, FIG. 4 shows a fluorescence spectrum, consistent with one or more exemplary embodiments of the present disclosure. An exemplary fluorescence spectrum 400 may include a first pair of fluorescence peaks and a second pair of peak wavelengths. In an exemplary embodiment, the first pair may include a first fluorescence peak $I_{w1}$ and a second fluorescence peak $I_{w2}$. In an exemplary embodiment, the second pair may include a first peak wavelength $w_1$ and a second peak wavelength $w_2$. In an exemplary embodiment, first peak wavelength $w_1$ may be smaller than second peak wavelength $w_2$. For example, for a sample of honey made from Ziziphus (i.e., Ziziphus is the floral source of honey) first peak wavelength $w_1$ may be about 485 nm and second peak wavelength $w_2$ may be about 545 nm. In an exemplary embodiment, first peak wavelength $w_1$ may be associated with first fluorescence peak $I_{w1}$. In an exemplary embodiment, an amplitude of fluorescence spectrum 400 may be equal to first fluorescence peak $I_{w1}$ at first peak wavelength $w_1$. In an exemplary embodiment, second peak wavelength $w_2$ may be associated with second fluorescence peak $I_{w2}$. In an exemplary embodiment, an amplitude of fluorescence spectrum 400 may be equal to second fluorescence peak $I_{w2}$ at second peak wavelength $w_2$.

Referring to FIGS. 1A, 2, and 4, in an exemplary embodiment, computer system 214 may be utilized for detecting the first pair in step 108. In an exemplary embodiment, detecting the first pair may include detecting first fluorescence peak $I_{w1}$ and second fluorescence peak $I_{w2}$ in fluorescence spectrum 400. In an exemplary embodiment, each of first fluorescence peak $I_{w1}$ and second fluorescence peak $I_{w2}$ may include a respective local maximum fluorescence intensity in fluorescence spectrum 400. Therefore, in an exemplary embodiment, each of first fluorescence peak $I_{w1}$ and second fluorescence peak $I_{w2}$ may be detected by finding respective local maxima of the curve of fluorescence spectrum 400.

In an exemplary embodiment, computer system 214 may be utilized for detecting the second pair in step 108. In an exemplary embodiment, detecting the second pair may include detecting first peak wavelength $w_1$ and second peak wavelength $w_2$ in fluorescence spectrum 400. In an exemplary embodiment, first peak wavelength $w_1$ may be associated with first fluorescence peak $I_{w1}$ and second peak wavelength $w_2$ may be associated with second fluorescence peak $I_{w2}$. In an exemplary embodiment, each of first peak wavelength $w_1$ and second peak wavelength $w_2$ may be detected by locating a wavelength at which the amplitude of fluorescence spectrum 400 reaches first fluorescence peak $I_{w1}$ and second fluorescence peak $I_{w2}$, respectively.

Figure 1C:
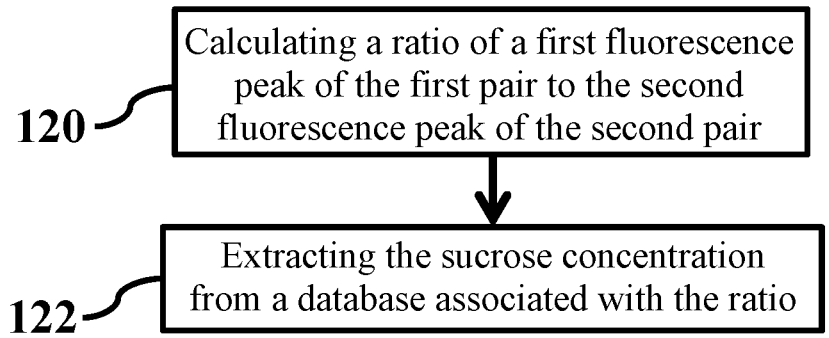
FIG. 1C shows a flowchart for determining sucrose concentration, consistent with one or more exemplary embodiments of the present disclosure.

In further detail with regards to step 110, FIG. 1C shows a flowchart for determining sucrose concentration, consistent with one or more exemplary embodiments of the present disclosure. In an exemplary embodiment, computer system 214 may be utilized for determining sucrose concentration. In an exemplary embodiment, determining the sucrose concentration may include calculating a ratio of first fluorescence peak $I_{w1}$ to second fluorescence peak $I_{w2}$ (step 120) and extracting the sucrose concentration from the database by finding a first predetermined sucrose concentration of a plurality of predetermined sucrose concentrations in the database (step 122). An exemplary first predetermined sucrose concentration may be associated with the ratio.

For further detail with respect to step 120, in an exemplary embodiment, a ratio $$\frac{I_{w1}}{I_{w2}}$$

may be calculated by dividing a value of first fluorescence peak $I_{w1}$ by a value of second fluorescence peak $I_{w2}$. According to experimental studies, although the shape of fluorescence spectrum or fluorescence peak values may depend on environmental conditions (such as temperature, humidity, etc.), ratio $$\frac{I_{w1}}{I_{w2}}$$

may remain almost unchanged at different environmental conditions for a fixed amount of sucrose concentration. Therefore, in an exemplary embodiment, ratio $$\frac{I_{w1}}{I_{w2}}$$

may be utilized for determining sucrose concentration in sample 302.

Figure 5:
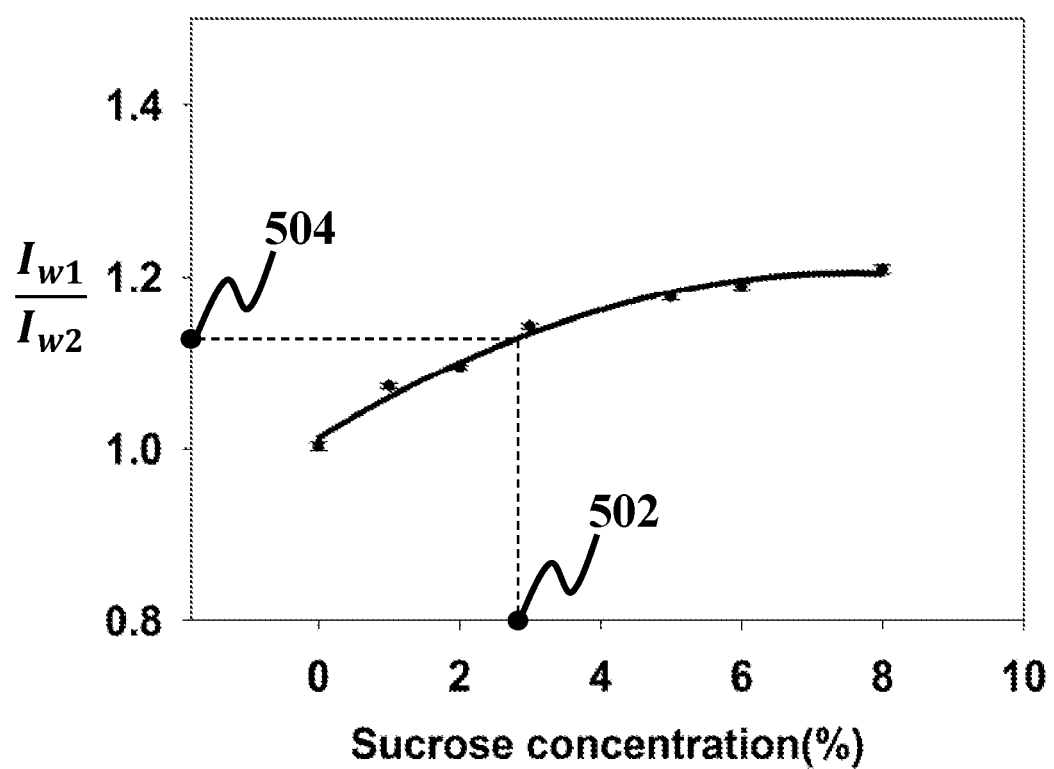
FIG. 5 shows a diagram for variations of fluorescence peak ratio with sucrose concentration, consistent with one or more exemplary embodiments of the present disclosure.

In further detail regarding step 122, FIG. 5 shows a diagram for variations of fluorescence peak ratio with sucrose concentration, consistent with one or more exemplary embodiments of the present disclosure. An exemplary diagram 500 may present a one-to-one relationship between ratio $$\frac{I_{w1}}{I_{w2}}$$

and sucrose concentration. In an exemplary embodiment, diagram 500 may be stored in the database. An exemplary database may include several diagrams similar to diagram 500 for different types of honey that may be made from different floral sources. In an exemplary embodiment, diagram 500 may present values of ratio $$\frac{I_{w1}}{I_{w2}}$$

for each of the plurality of predetermined sucrose concentrations. Therefore, in an exemplary embodiment, the sucrose concentration in sample 302 may be extracted from diagram 500 in step 122 by locating a predetermined sucrose concentration that may correspond to the value of ratio $$\frac{I_{w1}}{I_{w2}}$$

in diagram 500. For example, a first predetermined sucrose concentration 502 may correspond to a value 504 of ratio $$\frac{I_{w1}}{I_{w2}}.$$

In an exemplary embodiment, first predetermined sucrose concentration 502 may also be associated with the first peak wavelength. In an exemplary embodiment, the first peak wavelength may shift toward lower wavelengths as the sucrose concentration of honey increases. As a result, in an exemplary embodiment, first fluorescence peak $I_{w1}$ may appear at a shifted wavelength for an increased sucrose concentration. Therefore, in an exemplary embodiment, the sucrose concentration in sample 302 may be obtained by finding a predetermined sucrose concentration in the database (for example, first predetermined sucrose concentration 502) that corresponds to the shifted wavelength.

In an exemplary embodiment, determining the sucrose concentration may further include extracting the sucrose concentration from the database by finding a second predetermined sucrose concentration of the plurality of predetermined sucrose concentrations in the database. In an exemplary embodiment, the second predetermined sucrose concentration may be associated with the first peak wavelength. In an exemplary embodiment, the first peak wavelength may shift toward lower wavelengths as the sucrose concentration of honey increases. As a result, in an exemplary embodiment, first fluorescence peak $I_{w1}$ may appear at a shifted wavelength for an increased sucrose concentration. An exemplary second predetermined sucrose concentration may correspond to the shifted wavelength. Therefore, in an exemplary embodiment, two predetermined sucrose concentrations may be available for determining the sucrose concentration in sample 302. An exemplary first predetermined sucrose concentration may correspond to ratio $$\frac{I_{w1}}{I_{w2}}$$

and an exemplary second predetermined sucrose concentration may correspond to a shifted value of first peak wavelength $w_1$. Therefore, in an exemplary embodiment, determining the sucrose concentration may further include estimating the sucrose concentration based on the both first predetermined sucrose concentration and the second predetermined sucrose concentration. An exemplary estimated sucrose concentration may be obtained by averaging the first predetermined sucrose concentration and the second predetermined sucrose concentration.

In an exemplary embodiment, determining the sucrose concentration utilizing the database may further include generating the database utilizing a standard sample of honey. An exemplary standard sample may be made from a validated same floral source that may be claimed to be the source of sample 302, that is, it may be confirmed that the validated floral source is genuine. Therefore, the database may be utilized as a measure to validate originality and purity of sample 302, as well as determining an amount of additional sucrose concentration in sample 302 with respect to the standard sample.

Figure 1D:
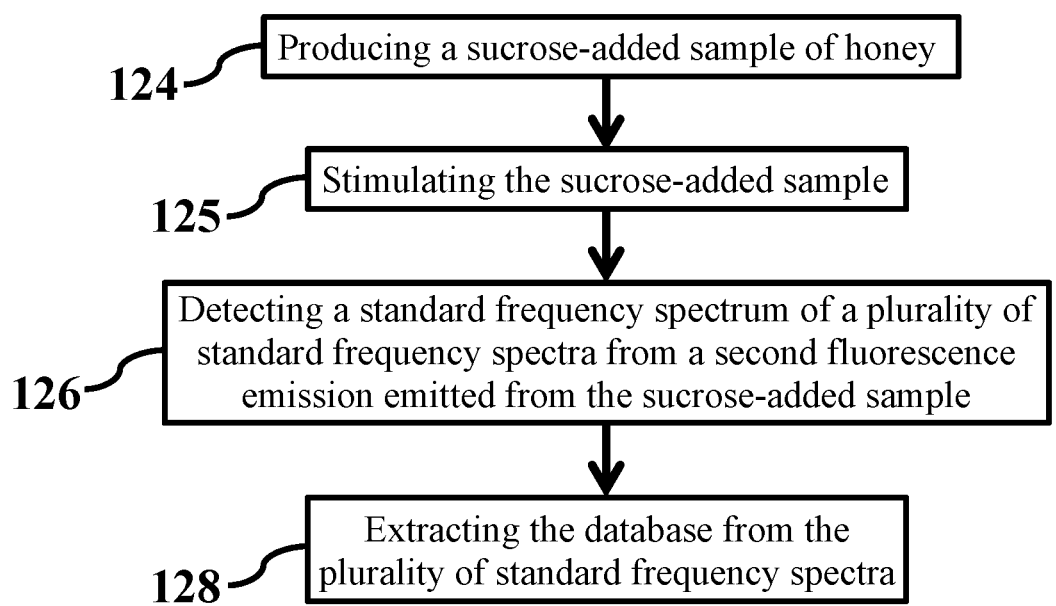
FIG. 1D shows a flowchart for generating a database, consistent with one or more exemplary embodiments of the present disclosure.

FIG. 1D shows a flowchart for generating a database, consistent with one or more exemplary embodiments of the present disclosure. In an exemplary embodiment, generating the database may include producing a sucrose-added sample of honey (step 124), stimulating the sucrose-added sample (step 125), detecting a standard fluorescence spectrum of a plurality of standard fluorescence spectra from a second fluorescence emission (step 126), and extracting the database from the plurality of standard fluorescence spectra (step 128).

In further detail regarding step 124, in an exemplary embodiment, the sucrose-added sample of honey may be produced by adding a predetermined sucrose concentration of the plurality of predetermined sucrose concentrations to the standard sample. Referring again to FIG. 5, in an exemplary embodiment, predetermined sucrose concentration 502 may be added to the standard sample to produce the sucrose-added sample.

For further detail with respect to step 125, stimulating the sucrose-added sample may include emitting a second laser beam on the sucrose-added sample in a second stimulation direction. In an exemplary embodiment, stimulation conditions in step 125 may be set similar to conditions in step 104. In other words, in an exemplary embodiment, sample 302 and the sucrose-added sample may be stimulated in similar conditions so that stimulation results may be affected only by a difference in sucrose concentration between sample 302 and the sucrose-added sample. Therefore, in an exemplary embodiment, laser 202 may be utilized for emitting a second laser beam and a wavelength of second laser beam may be set equal to the laser wavelength of the first laser beam. In an exemplary embodiment, laser 202 may include laser diode that may be configured to emit a violet laser beam. In an exemplary embodiment, the power of laser 202 may be set to about 20-60 mW so that the second laser beam intensity may be high enough to stimulate the sucrose-added sample.

In further detail with regards to step 126, in an exemplary embodiment, the second fluorescence emission may be emitted from the sucrose-added sample in a second detection direction. In an exemplary embodiment, detection conditions in step 126 may be set similar to conditions in step 106. In other words, in an exemplary embodiment, the first fluorescence emission form sample 302 and the second fluorescence emission from the sucrose-added sample may be detected in similar conditions so that detection results may be affected only by a difference in sucrose concentration between sample 302 and the sucrose-added sample.

Therefore, in an exemplary embodiment, tip 308 of optical fiber 210 may be utilized to capture the second fluorescence emission in a configuration similar to the configuration of FIG. 3. Therefore, an exemplary angle between the second detection and the second stimulation direction may be equal to detection angle θ. An exemplary second fluorescence emission may be sent by optical fiber 210 to spectrometer 208. In an exemplary embodiment, spectrometer 208 may be utilized for detecting the standard fluorescence spectrum. In an exemplary embodiment, each of the plurality of standard fluorescence spectra may be associated with a respective predetermined sucrose concentration of the plurality of predetermined sucrose concentrations.

Figure 6:
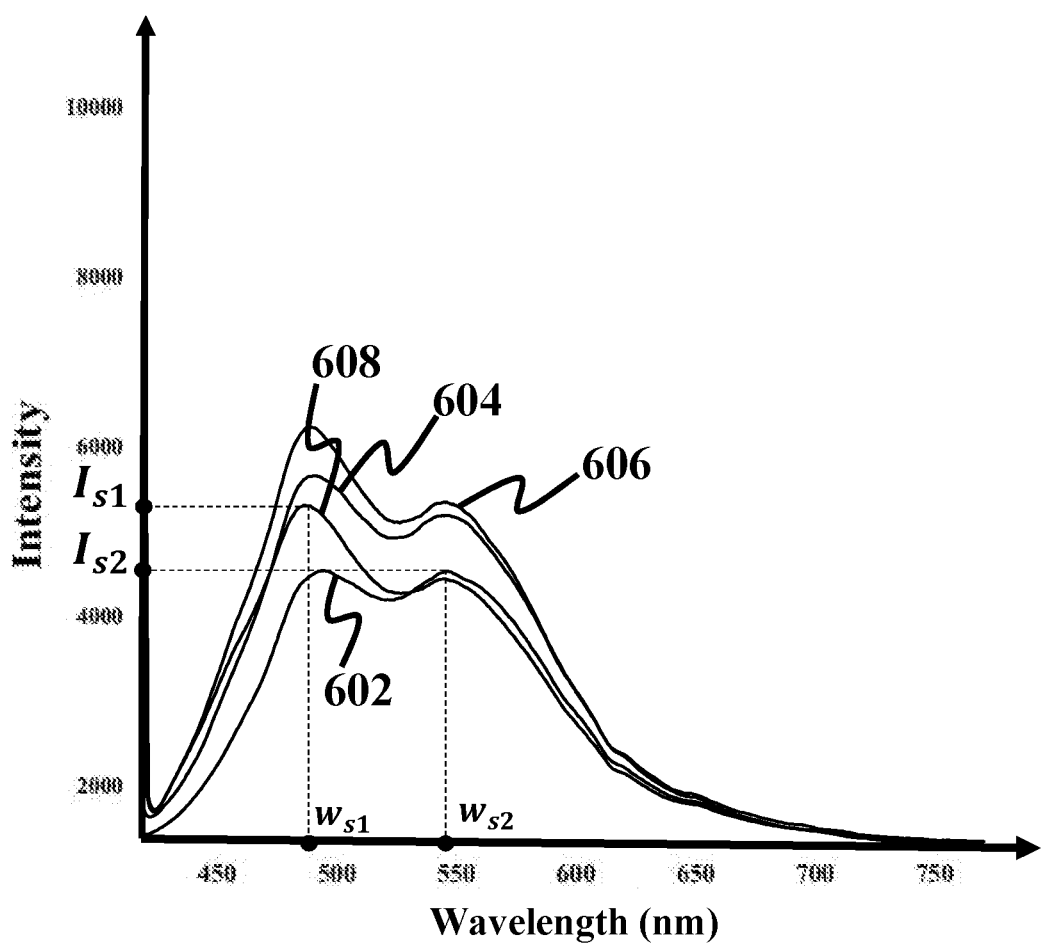
FIG. 6 shows a plurality of standard fluorescence spectra, consistent with one or more exemplary embodiments of the present disclosure.

FIG. 6 shows a plurality of standard fluorescence spectra, consistent with one or more exemplary embodiments of the present disclosure. In an exemplary embodiment, for each of the plurality of predetermined sucrose concentrations, a separate standard fluorescence spectrum may be detected. For example, a standard fluorescence spectrum 602, a standard fluorescence spectrum 604, a standard fluorescence spectrum 606, and standard fluorescence spectrum 608 may be detected from emissions from sucrose-added samples of honey with 0% (i.e., the standard sample without extra sucrose), 2%, 5%, and 8% sucrose concentrations. Referring again to FIG. 4, in an exemplary embodiment, a shape of each of plurality of standard fluorescence spectra 600 may be similar to the shape of fluorescence spectrum 400. In an exemplary embodiment, each of plurality of standard fluorescence spectra 600 may have two peaks similar to fluorescence spectrum 400.

Figure 1E:
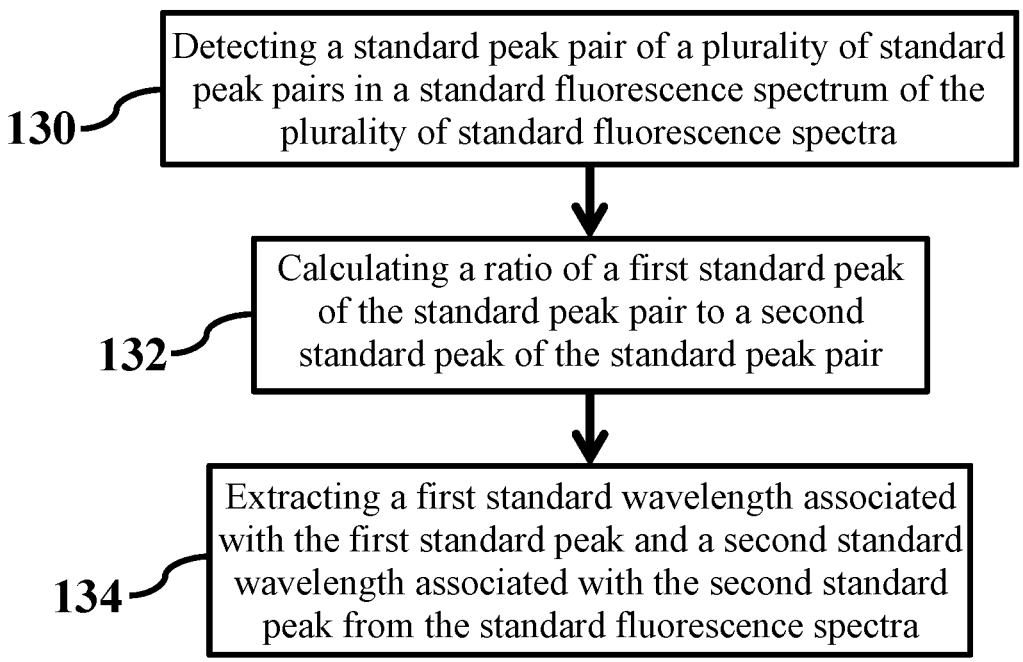
FIG. 1E shows a flowchart for extracting a database from a standard fluorescence spectrum, consistent with one or more exemplary embodiments of the present disclosure.

For further detail regarding step 128, FIG. 1E shows a flowchart for extracting a database from a standard fluorescence spectrum, consistent with one or more exemplary embodiments of the present disclosure. In an exemplary embodiment, extracting the database may include detecting a standard peak pair of a plurality of standard peak pairs in a standard fluorescence spectrum (step 130) and calculating a ratio of the first standard peak to the second standard peak (step 132).

Referring again to FIGS. 4 and 6, in an exemplary embodiment, the standard peak pair may include a first standard peak $I_{s1}$ and a second standard peak $I_{s2}$. In an exemplary embodiment, each of first standard peak $I_{s1}$ and second standard peak $I_{s2}$ may include a respective local maximum fluorescence intensity in a respective standard fluorescence spectrum. In an exemplary embodiment, first standard peak $I_{s1}$ may be analogous to first fluorescence peak $I_{w1}$ and second standard peak $I_{s2}$ may be analogous to second fluorescence peak $I_{w2}$. In an exemplary embodiment, details of detecting the standard peak pair in step 130 may be similar to detecting the first pair of fluorescence peaks in step 108, as described above.

In further detail with respect to step 132, in an exemplary embodiment, a ratio $$\frac{I_{s1}}{I_{s2}}$$

of first standard peak $I_{s1}$ to the second standard peak $I_{s2}$ may be associated with a respective predetermined sucrose concentration. In an exemplary embodiment, ratio $$\frac{I_{w1}}{I_{w2}}$$

of first fluorescence peak $I_{w1}$ to second fluorescence peak $I_{w2}$ may be approximately equal to ratio $$\frac{I_{s1}}{I_{s2}}$$

if sample 302 has a same floral source as the standard sample and a same level of sucrose concentration as the sucrose-added sample. Therefore, in an exemplary embodiment, sucrose concentration of sample 302 may be determined by finding a predetermined sucrose concentration that may correspond to ratio $$\frac{I_{w1}}{I_{w2}}.$$

Referring again to FIG. 5, in an exemplary embodiment, for each of the plurality of predetermined sucrose concentrations, a respective ratio of the first standard peak to the second standard peak may be calculated to obtain diagram 500. In an exemplary embodiment, further details of calculating ratio $$\frac{I_{s1}}{I_{s2}}$$

may be similar to calculating ratio $$\frac{I_{w1}}{I_{w2}}$$

in step 120, as described above.

Referring again to FIG. 1E, in an exemplary embodiment, extracting the database in step 128 may further include extracting a first standard wavelength and a second standard wavelength from a respective standard fluorescence spectrum (step 134). Referring again to FIG. 6, an exemplary first standard wavelength $w_{s1}$ may be associated with first standard peak $I_{s1}$ and an exemplary second standard wavelength $w_{s2}$ may be associated with second standard peak $I_{s2}$. In an exemplary embodiment, an amplitude of standard fluorescence spectrum 608 may be equal to first fluorescence peak $I_{w1}$ at first standard wavelength $w_{s1}$. In an exemplary embodiment, an amplitude of standard fluorescence spectrum 608 may be equal to second standard peak $I_{s2}$ at second standard wavelength $w_{s2}$. In an exemplary embodiment, first standard wavelength $w_{s1}$ may be smaller than second standard wavelength $w_{s2}$. In an exemplary embodiment, details of extracting first standard wavelength $w_{s1}$ and second standard wavelength $w_{s2}$ in step 134 may be similar to detecting the second pair of peak wavelengths in step 108, as described above.

Referring again to FIGS. 4 and 6, in an exemplary embodiment, first standard wavelength $w_{s1}$ may be shifted toward lower wavelengths due to a higher sucrose concentration in the sucrose-added sample compared to the standard sample, as discussed above. In an exemplary embodiment, the spectral shift of first standard wavelength $w_{s1}$ may have a one-to-one relationship with the level of sucrose concentration in the sucrose-added sample. As a result, in an exemplary embodiment, sucrose concertation of sample 302 and the sucrose-added sample may be equal if first peak wavelength $w_1$ and first and standard wavelength $w_{s1}$ are equal. Therefore, in an exemplary embodiment, sucrose concertation of sample 302 may be determined by finding a standard fluorescence spectrum in plurality of standard fluorescence spectra 600 that may have a first standard wavelength equal to first peak wavelength $w_1$. In an exemplary embodiment, the sucrose concentration of sample 302 may be determined equal to a predetermined sucrose concentration corresponding to the standard fluorescence spectrum.

Figure 7:
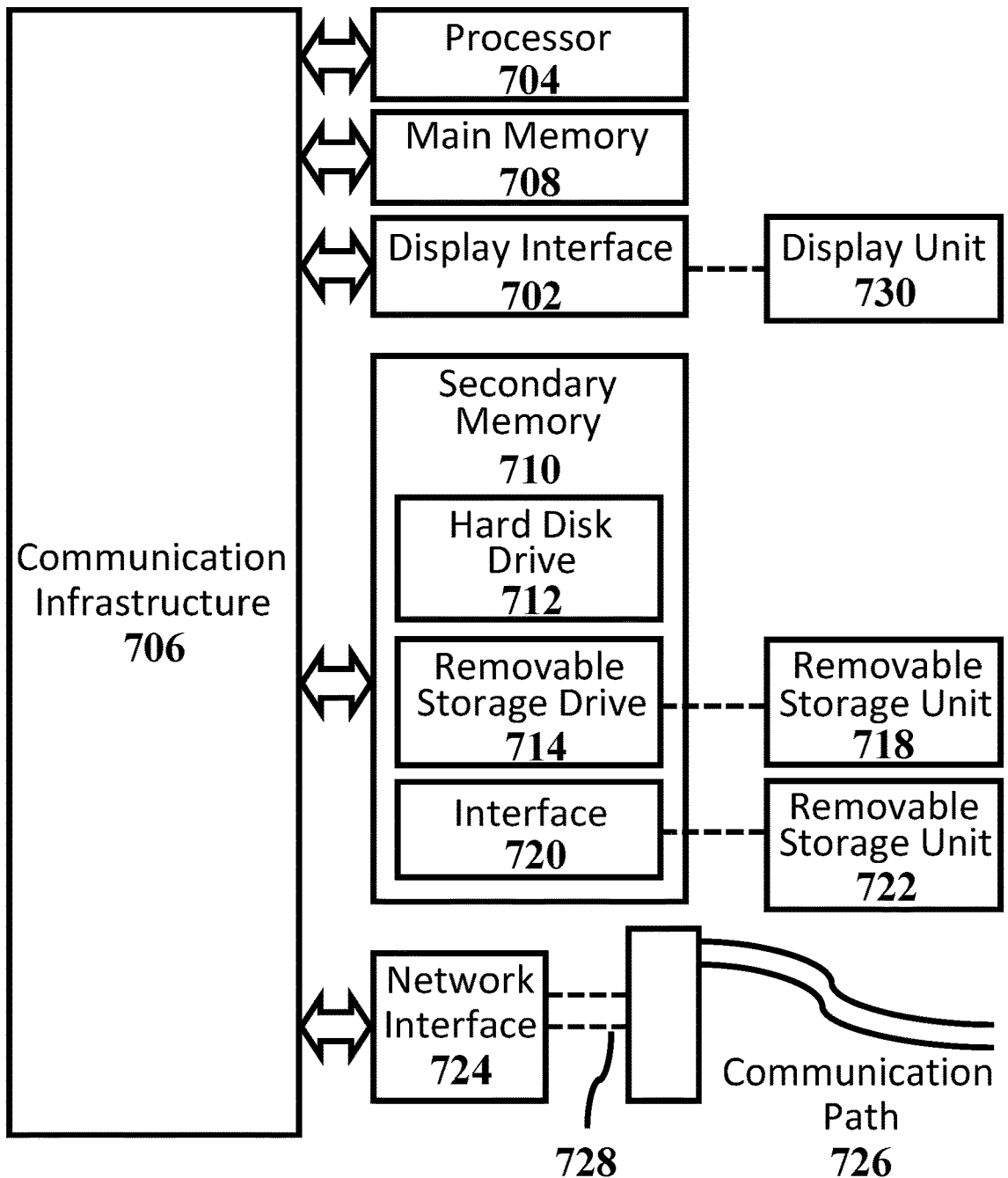
FIG. 7 shows a high-level functional block diagram of a computer system, consistent with one or more exemplary embodiments of the present disclosure.

FIG. 7 shows an example computer system in which an embodiment of the present invention, or portions thereof, may be implemented as computer-readable code, consistent with exemplary embodiments of the present disclosure. An exemplary computer system 700 may be analogous to computer system 214. In an exemplary embodiment, steps 108-110 and 126-128 of method 100 may be implemented in computer system 700 using hardware, software, firmware, tangible computer readable media having instructions stored thereon, or a combination thereof and may be implemented in one or more computer systems or other processing systems. Hardware, software, or any combination of such may embody any of the modules and components in FIGS. 1A-2.

If programmable logic is used, such logic may execute on a commercially available processing platform or a special purpose device. One ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the invention is described in terms of this example computer system 500. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 704 may be a special purpose or a general-purpose processor device. As will be appreciated by persons skilled in the relevant art, processor device 704 may also be a single processor in a multi-core/multiprocessor system, such system operating alone, or in a cluster of computing devices operating in a cluster or server farm. Processor device 704 may be connected to a communication infrastructure 706, for example, a bus, message queue, network, or multi-core message-passing scheme.

In an exemplary embodiment, computer system 700 may include a display interface 502, for example a video connector, to transfer data to a display unit 730, for example, a monitor. Computer system 700 may also include a main memory 708, for example, random access memory (RAM), and may also include a secondary memory 710. Secondary memory 710 may include, for example, a hard disk drive 712, and a removable storage drive 714. Removable storage drive 714 may include a floppy disk drive, a magnetic tape drive, an optical disk drive, a flash memory, or the like. Removable storage drive 714 may read from and/or write to a removable storage unit 718 in a well-known manner. Removable storage unit 718 may include a floppy disk, a magnetic tape, an optical disk, etc., which may be read by and written to by removable storage drive 714. As will be appreciated by persons skilled in the relevant art, removable storage unit 718 may include a computer usable storage medium having stored therein computer software and/or data.

In alternative implementations, secondary memory 710 may include other similar means for allowing computer programs or other instructions to be loaded into computer system 700. Such means may include, for example, a removable storage unit 722 and an interface 720. Examples of such means may include a program cartridge and cartridge interface (such as that found in video game devices), a removable memory chip (such as an EPROM, or PROM) and associated socket, and other removable storage units 722 and interfaces 720 which allow software and data to be transferred from removable storage unit 722 to computer system 700.

Computer system 700 may also include a communications interface 724. Communications interface 724 allows software and data to be transferred between computer system 700 and external devices. Communications interface 724 may include a modem, a network interface (such as an Ethernet card), a communications port, a PCMCIA slot and card, or the like. Software and data transferred via communications interface 724 may be in the form of signals, which may be electronic, electromagnetic, optical, or other signals capable of being received by communications interface 724. These signals may be provided to communications interface 724 via a communications path 726. Communications path 726 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 718, removable storage unit 722, and a hard disk installed in hard disk drive 712. Computer program medium and computer usable medium may also refer to memories, such as main memory 508 and secondary memory 710, which may be memory semiconductors (e.g. DRAMs, etc.).

Computer programs (also called computer control logic) are stored in main memory 708 and/or secondary memory 710. Computer programs may also be received via communications interface 724. Such computer programs, when executed, enable computer system 700 to implement different embodiments of the present disclosure as discussed herein. In particular, the computer programs, when executed, enable processor device 704 to implement the processes of the present disclosure, such as the operations in method 100 illustrated by flowchart 100 of FIG. 1A discussed above. Accordingly, such computer programs represent controllers of computer system 700. Where an exemplary embodiment of method 100 is implemented using software, the software may be stored in a computer program product and loaded into computer system 700 using removable storage drive 714, interface 720, and hard disk drive 712, or communications interface 724.

Embodiments of the present disclosure also may be directed to computer program products including software stored on any computer useable medium. Such software, when executed in one or more data processing device, causes a data processing device to operate as described herein. An embodiment of the present disclosure may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nano-technological storage device, etc.).

The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for determining sucrose concentration in honey based on fluorescence spectroscopy, the method comprising:

preparing a sample of honey associated with a floral source;

stimulating the sample by emitting a first laser beam on the sample in a first stimulation direction, the first laser beam comprising a laser wavelength;

detecting, utilizing a spectrometer, a fluorescence spectrum from a first fluorescence emission emitted from the sample in a first detection direction making a detection angle with the stimulation direction;

detecting, utilizing one or more processors, a first pair of fluorescence peaks and a second pair of peak wavelengths in the fluorescence spectrum by:

detecting a first fluorescence peak of the first pair and a second fluorescence peak of the first pair in the fluorescence spectrum, each of the first fluorescence peak and the second fluorescence peak comprising a respective local maximum fluorescence intensity in the fluorescence spectrum; and detecting a first peak wavelength of the second pair and a second peak wavelength of the second pair in the fluorescence spectrum, the first peak wavelength associated with the first fluorescence peak and the second peak wavelength associated with the second fluorescence peak, the first peak wavelength smaller than the second peak wavelength; and determining, utilizing the one or more processors, a sucrose concentration based on one of the first pair and the second pair utilizing a database comprising a plurality of predetermined sucrose concentrations associated with the one of the first pair and the second pair.

2. The method of claim 1, wherein determining the sucrose concentration comprises:
calculating a ratio of the first fluorescence peak to the second fluorescence peak;
finding a first predetermined sucrose concentration of the plurality of predetermined sucrose concentrations in the database, the predetermined sucrose concentration associated with the ratio;
finding a second predetermined sucrose concentration of the plurality of predetermined sucrose concentrations in the database, the predetermined sucrose concentration associated with the first peak wavelength; and
estimating the sucrose concentration by averaging the first predetermined sucrose concentration and the second predetermined sucrose concentration.

3. The method of claim 1, wherein determining the sucrose concentration comprises:
calculating a ratio of the first fluorescence peak to the second fluorescence peak; and
extracting the sucrose concentration from the database by finding a predetermined sucrose concentration of the plurality of predetermined sucrose concentrations in the database, the predetermined sucrose concentration associated with the ratio.

4. The method of claim 1, wherein determining the sucrose concentration comprises extracting the sucrose concentration from the database by finding a predetermined sucrose concentration of the plurality of predetermined sucrose concentrations in the database, the predetermined sucrose concentration associated with the first peak wavelength.

5. The method of claim 1, wherein determining the sucrose concentration utilizing the database comprises generating the database utilizing a standard sample of honey, the standard sample made from the floral source.

6. The method of claim 5, wherein generating the database comprises:
producing a sucrose-added sample of honey by adding a predetermined sucrose concentration of the plurality of predetermined sucrose concentrations to the standard sample;
stimulating the sucrose-added sample by emitting a second laser beam on the sucrose-added sample in a second stimulation direction, the second laser beam comprising the laser wavelength;
detecting, utilizing the spectrometer, a standard fluorescence spectrum of a plurality of standard fluorescence spectra from a second fluorescence emission emitted from the sucrose-added sample in a second detection direction making the detection angle with the second stimulation direction, each of the plurality of standard fluorescence spectra associated with a respective predetermined sucrose concentration of the plurality of predetermined sucrose concentrations; and
extracting the database from the plurality of standard fluorescence spectra.

7. The method of claim 6, wherein extracting the database comprises:
detecting, utilizing the one or more processors, a standard peak pair of a plurality of standard peak pairs in the standard fluorescence spectrum, the standard peak pair comprising a first standard peak and a second standard peak, each of the first standard peak and the second standard peak comprising a respective local maximum fluorescence intensity in the standard fluorescence spectrum; and
calculating a ratio of the first standard peak to the second standard peak, the ratio associated with the predetermined sucrose concentration.

8. The method of claim 7, wherein extracting the database further comprises extracting a first standard wavelength associated with the first standard peak and a second standard wavelength associated with the second standard peak from the standard fluorescence spectrum, the first standard wavelength smaller than the second standard wavelength.

9. The method of claim 1, wherein preparing the sample comprises depositing the sample in a cylindrical container, a diameter of a cross-section of the cylindrical container equal to or larger than a width of the first laser beam.

10. The method of claim 1, wherein detecting the florescence spectrum comprises:
setting, utilizing a goniometer, the detection angle in a range of 20° and 90°;
positioning, utilizing a moving table, a main axis of a tip of an optical fiber in the first detection direction;
capturing the first fluorescence emission by the optical fiber; and
sending the first fluorescence emission to the spectrometer via the optical fiber.

11. The method of claim 1, wherein emitting the first laser beam comprises setting the laser wavelength in a range of 390 nm and 410 nm.

12. A system for determining sucrose concentration in honey based on fluorescence spectroscopy, the system comprising:
a laser configured to stimulate a sample of honey associated with a floral source by emitting a first laser beam on the sample in a first stimulation direction, the first laser beam comprising a laser wavelength;
an optical filter configured to set a width of the first laser beam;
a cylindrical container configured to contain the sample;
a spectrometer configured to detect a fluorescence spectrum from a first fluorescence emission emitted from the sample in a first detection direction making a detection angle with the stimulation direction;
an optical fiber configured to:
capture the first fluorescence emission; and
send the first fluorescence emission to the spectrometer;
a moving table configured to position a main axis of a tip of the optical fiber in the first detection direction, the moving table comprising goniometer configured to set the detection angle;
a memory having processor-readable instructions stored therein; and
one or more processors configured to access the memory and execute the processor-readable instructions, which, when executed by the processor configures the one or more processors to perform a method, the method comprising:
detecting a first pair of fluorescence peaks and a second pair of peak wavelengths in the fluorescence spectrum by:
detecting a first fluorescence peak of the first pair and a second fluorescence peak of the first pair in the fluorescence spectrum, each of the first fluorescence peak and the second fluorescence peak comprising a respective local maximum fluorescence intensity in the fluorescence spectrum; and detecting a first peak wavelength of the second pair and a second peak wavelength of the second pair in the fluorescence spectrum, the first peak wavelength associated with the first fluorescence peak and the second peak wavelength associated with the second fluorescence peak; and determining a sucrose concentration based on one of the first pair and the second pair utilizing a database comprising a plurality of predetermined sucrose concentrations associated with the one of the first pair and the second pair.

13. The system of claim 12, wherein determining the sucrose concentration comprises:

calculating a ratio of the first fluorescence peak to the second fluorescence peak;

finding a first predetermined sucrose concentration of the plurality of predetermined sucrose concentrations in the database, the predetermined sucrose concentration associated with the ratio;

finding a second predetermined sucrose concentration of the plurality of predetermined sucrose concentrations in the database, the predetermined sucrose concentration associated with the first peak wavelength; and estimating the sucrose concentration by averaging first predetermined sucrose concentration and the second predetermined sucrose concentration.

14. The system of claim 12, wherein determining the sucrose concentration comprises:

calculating a ratio of the first fluorescence peak to the second fluorescence peak; and extracting the sucrose concentration from the database by finding a predetermined sucrose concentration of the plurality of predetermined sucrose concentrations in the database, the predetermined sucrose concentration associated with the ratio.

15. The system of claim 12, wherein determining the sucrose concentration comprises extracting the sucrose concentration from the database by finding a predetermined sucrose concentration of the plurality of predetermined sucrose concentrations in the database, the predetermined sucrose concentration associated with the first peak wavelength.

16. The system of claim 12, wherein determining the sucrose concentration utilizing the database comprises generating the database utilizing a standard sample of honey, the standard sample made from the floral source.

17. The system of claim 16, wherein generating the database comprises:

producing a sucrose-added sample of honey by adding a predetermined sucrose concentration of the plurality of predetermined sucrose concentrations to the standard sample;

stimulating, utilizing the laser, the sucrose-added sample by emitting a second laser beam on the sucrose-added sample in a second stimulation direction, the second laser beam comprising the laser wavelength;

detecting, utilizing the spectrometer, a standard fluorescence spectrum of a plurality of standard fluorescence spectra from a second fluorescence emission emitted from the sucrose-added sample in a second detection direction making the detection angle with the second stimulation direction, each of the plurality of standard fluorescence spectra associated with a respective predetermined sucrose concentration of the plurality of predetermined sucrose concentrations; and extracting the database from the plurality of standard fluorescence spectra.

18. The system of claim 17, wherein extracting the database comprises:

detecting a standard peak pair of a plurality of standard peak pairs in the standard fluorescence spectrum, the standard peak pair comprising a first standard peak and a second standard peak, each of the first standard peak and the second standard peak comprising a respective local maximum fluorescence intensity in the standard fluorescence spectrum; and calculating a ratio of the first standard peak to the second standard peak, the ratio associated with the predetermined sucrose concentration.

19. The system of claim 18, wherein extracting the database further comprises extracting a first standard wavelength associated with the first standard peak and a second standard wavelength associated with the second standard peak from the standard fluorescence spectrum, the first standard wavelength smaller than the second standard wavelength.

20. The system of claim 12, wherein:

the optical filter is further configured to set a width of the first laser beam equal to or smaller than a diameter of a cross-section of the cylindrical container;

the goniometer is further configured to set the detection angle in a range of 20° and 90°; and the laser wavelength is set in a range of 390 nm and 410 nm.

* * * * *